(12) United States Patent
Chodorowski-Kimmes

(10) Patent No.: US 8,003,086 B2
(45) Date of Patent: Aug. 23, 2011

(54) BIS-UREA COMPOUNDS AND COMPOSITIONS AND METHOD OF COSMETIC TREATMENT

(75) Inventor: Sandrine Chodorowski-Kimmes, Senlis (FR)

(73) Assignee: L'Oreal S.A., Paris (FR)

( * ) Notice: Subject to any disclaimer, the term of this patent is extended or adjusted under 35 U.S.C. 154(b) by 815 days.

(21) Appl. No.: 11/797,931

(22) Filed: May 9, 2007

(65) Prior Publication Data

US 2007/0274934 A1    Nov. 29, 2007

Related U.S. Application Data

(60) Provisional application No. 60/802,108, filed on May 22, 2006.

(30) Foreign Application Priority Data

May 9, 2006   (FR) .................................. 06 51653

(51) Int. Cl.
   *A61Q 1/02*   (2006.01)
   *A61Q 19/00*   (2006.01)
(52) U.S. Cl. .................... 424/70.12; 514/740; 514/741; 514/63; 424/70.1; 424/401
(58) Field of Classification Search .......................... None
   See application file for complete search history.

(56) References Cited

U.S. PATENT DOCUMENTS

| 3,726,907 A | 4/1973 | Tesoro et al. |
| 4,062,693 A | 12/1977 | Berger |
| 2003/0091520 A1 * | 5/2003 | Livoreil et al. ............... 424/70.1 |
| 2005/0245673 A1 | 11/2005 | Ferrari et al. |

FOREIGN PATENT DOCUMENTS

| EP | 0 406 731 A2 | 1/1991 |
| JP | 10-236981 | 9/1998 |
| JP | 2003-64346 | 3/2003 |
| JP | 2004-182692 | 7/2004 |
| JP | 2004-182693 | 7/2004 |
| JP | 2004-262856 | 9/2004 |
| WO | WO 97/36572 | 10/1997 |
| WO | WO 02/47628 | 6/2002 |
| WO | WO 03/105801 A1 | 12/2003 |
| WO | WO 2004/052963 A1 | 6/2004 |

OTHER PUBLICATIONS

Colombani et al, Selective synthesis of non-symmetrical bis-ureas and their self-assembly, (Nov. 2004).*
Moreau et al, Nanostructuring organo-silicas: combination of intermolecular interactions and molecular recognition properties to generate self-assembled hybrids with phenylene or adenine . . . thymine bridging units, (May 2005).*
Mel'nik et al, Synthesis of Alkoxysilanes as Starting Substances for Preparation of New Materials by the Sol Gel Procedure Silanes with Urea Functional Group, (2004).*
Sol-Gel: A Low Temperature Process for the Materials of the New Millennium by Jean Phalippou.*
Olivier Colombani et al., "Attempt toward 1D Cross-Linked Thermoplastic Elastomers: Structure and Mechanical Properties of a New System," Macromolecules, vol. 38, pp. 1752-1759 (2005).
Olivier Colombani et al., "Selective synthesis of non-symmetrical bis-ureas and their self-assembly," New J. Chem., vol. 28, pp. 1373-1382 (2004).
Frédéric Lortie et al., "Structural and Rheological Study of a Bis-urea Based Reversible Polymer in an Apolar Solvent," Langmuir, vol. 18, pp. 7218-7222 (2002).
Andrew J. Carr et al., "The Design of Organic Gelators: Solution and Solid State Properties of a Family of Bis-Ureas," Tetrahedron Letters, vol. 39, pp. 7447-7450 (1998).
Sylvie Boileau et al, "Soluble supramolecular polymers based on urea compounds," New J. Chem, vol. 24, pp. 845-848 (2000).
Vesna Simic et al., "Highly Cooperative Formation of Bis-Urea Based Supramolecular Polymers," J. Am. Chem. Soc., vol. 125, pp. 13145-13154 (2003).
English language abstract of JP 10-236981, Sep. 8, 1998.
English language abstract of JP 2003-64346, Mar. 5, 2003.
English language abstract of JP 2004-182692, Jul. 2, 2004.
English language abstract of JP 2004-182693, Jul. 2, 2004.
English language abstract of JP 2004-262856, Sep. 24, 2004.
French Search Report for FR 0651653, dated Feb. 16, 2007.

* cited by examiner

*Primary Examiner* — Anish Gupta
*Assistant Examiner* — Ryan C Smith
(74) *Attorney, Agent, or Firm* — Finnegan, Henderson, Farabow, Garrett & Dunner, LLP

(57) ABSTRACT

Disclosed herein is a cosmetic and/or pharmaceutical composition comprising, in a physiologically acceptable medium, a fatty phase and at least one compound chosen from compounds of formula (I), salts thereof, and isomers thereof, used to texture the fatty phase. Also disclosed herein is a method for texturing a cosmetic and/or pharmaceutical composition comprising adding to the composition at least one compound of formula (I). Further disclosed herein is a method for the cosmetic treatment of keratin materials comprising applying to the materials at least one composition of the present disclosure.

16 Claims, No Drawings

BIS-UREA COMPOUNDS AND COMPOSITIONS AND METHOD OF COSMETIC TREATMENT

This application claims benefit of U.S. Provisional Application No. 60/802,108, filed May 22, 2006, the contents of which are incorporated herein by reference. This application also claims benefit of priority under 35 U.S.C. §119 to French Patent Application No. FR 0651653, filed May 9, 2006, the contents of which are also incorporated herein by reference.

Disclosed herein are compositions, for instance, cosmetic or pharmaceutical compositions, having a liquid fatty phase textured with at least one bis-urea compound.

To structure oils and give them the desired texture or viscosity, the use of organogelling agents is known to persons skilled in the art. Organogelling agents are known as being small molecules capable of structuring an organic medium, at low concentration. They can modify the molecular interactions inside the oil and change its physical and/or chemical characteristics. However, the solubilization of these organogelling molecules in an oil or a mixture of oils often requires high temperatures, which can generate additional heating costs and/or be incompatible with the presence of heat-sensitive molecules. Furthermore, the gel thus obtained does not always have the required stability over time: the organogelling agent can precipitate and/or exude over time.

Several classes of organogelling agents are known to persons skilled in the art, including bis-urea compounds.

The use of certain bis-ureas as organogelling agent is described, for example, in International Patent Application Publication No. WO 02/47628, Japanese Patent Application No. 2003-064346, and Japanese Patent Nos. 08-237942 and 10-236981. These documents describe, for instance, the use of bis-ureas for texturing cosmetic or non-cosmetic media.

Various articles also describe organic molecules functionalized by at least one urea, for example, the articles by Bouteiller et al., in *New J. Chem.*, 2000, 24, 845-848; *Langmuir*, 2002, 18, 7218-7222, and *J. Am. Chem. Soc.* 2003, 125, 13148-13154, describing the use of certain bis-ureas in organic solvents such as toluene, carbon tetrachloride, and dodecane for the purpose of gelling the latter. Hanabusa et al. also describes the behavior of bis-urea molecules as organogelling agents (Langmuir 2003, 19(21), 8622-8624).

Additionally, the article by Hamilton et al. in *Tetrahedron Letters*, 1998, 39, 7447-7450 describes the ability of certain bis-urea derivatives to behave as gelling agents in certain organic solvents.

However, all the bis-ureas described in these documents are not solubilized at room temperature and/or in all cosmetic oils, for example, silicone oils, alone or as a mixture with carbon-based oils.

In the field of texturing of compositions comprising silicone oils or solvents, Japanese Patent Application No. 2004262856 describes silicone derivatives of amino acids, for instance, valine derivatives substituted with linear or graft PDMS chains capable of gelling the silicone oils without being limited by the other components of the formula.

Japanese Patent Application Nos. 2004182692 and 2004182693 also describe, as gelling agent, silicone oils, silicone-based bis-amide derivatives which may be cyclic or non-cyclic.

Still in the cosmetics field, International Patent Application Publication No. WO 97/36572 describes a cosmetic composition formed of an oil comprising at least one silicone unit and at least one gelling agent comprising at least one siloxane unit and at least one group forming hydrogen bonds.

Additionally, International Patent Application Publication No. WO 03/105801 describes a cosmetic composition comprising a fatty phase at least partially silicone-based and structured with a PDMS comprising at least two groups capable of forming an H bond.

International Patent Application Publication No. WO 2004/052963 also describes siloxane polymers comprising groups capable of forming at least 4 hydrogen bonds, and capable of gelling compositions, for example, cosmetic compositions.

Finally, International Patent Application Publication No. WO 2005/005557 describes, for instance, the use, as controlling agent in rheology, of an agent derived from the reaction between at least one polyisocyanate and at least one amine. The amine may contain a heteroatom.

In the non-cosmetic fields, European Patent No. 0 406 731 describes bis-urea molecules monofunctionalized by siloxane functional groups. This type of molecule is known in the field of adhesion and the treatment of surfaces, such as the surfaces of textiles.

However, none of these documents propose a chemical family comprising compounds capable of texturing, thickening, and/or gelling, a variety of cosmetic media such as media comprising carbon-based and/or hydrocarbon-based oils and/or solvents, silicone oils, and/or mixtures of carbon-based oils and silicone oils.

Thus, it would be desirable to provide such compounds which are capable of texturing and/or structuring nonaqueous cosmetic media, whether they comprise silicone and/or non-silicone (carbon-based) cosmetic oils.

It is known that, in order to identify a gelling compound capable of satisfactorily texturing a particular cosmetic composition and capable of being solubilized at room temperature in the oils of the composition, numerous tests must generally be performed beforehand.

A need therefore exists for texturing (or organogelling) compounds which may be described as universal in so far as they would be effective for texturing, at room temperature, a large number of silicone and non-silicone cosmetic oils, and mixtures thereof.

Disclosed herein are novel compounds capable of texturing, thickening, and/or gelling, cosmetic compositions, regardless of the nature of the oils which they comprise.

Also disclosed herein is a cosmetic and/or pharmaceutical composition comprising, in a physiologically acceptable medium, a fatty phase and at least one compound chosen from compounds of formula (I) as defined below, salts thereof, and isomers thereof.

Further disclosed herein is a method for texturing a cosmetic and/or pharmaceutical composition comprising, in a physiologically acceptable medium, a fatty phase, the method comprising adding to the composition at least one compound chosen from compounds of formula (I), salts thereof, and isomers thereof.

Still further disclosed herein are compounds of formula (Ia), salts thereof, and isomers thereof.

The present inventors have discovered that the bis-urea compounds defined herein, and mixtures thereof, are texturing, thickening, and/or gelling agents capable of satisfying the need for universal organogelling agents expressed above; for instance, the compounds of the present disclosure may be solubilized at room temperature in a large range of carbon-based and/or silicone cosmetic oils and solvents, and may make it possible to modify the viscosity of these oils and solvents even at low concentrations, such as less than 5% by weight.

Compounds

The bis-urea compounds of the present disclosure may be chosen from compounds of formula (I):

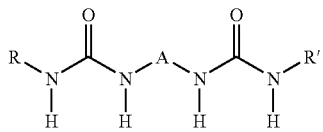

wherein:

A is a group of formula (II):

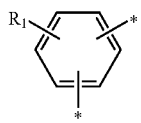

wherein $R_1$ is chosen from linear or branched $C_1$ to $C_4$ alkyl radicals, and * symbolizes the points of attachment of the group A to each of the two nitrogen atoms of the rest of the compound of formula (I), and R and R', which may be identical or different, are chosen from:

i) radicals of formula (III):

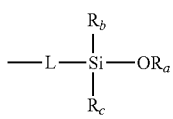

wherein:

L is chosen from single bonds and saturated or unsaturated, linear, branched, and/or cyclic, divalent carbon radicals, such as hydrocarbon (alkylene) radicals, comprising from 1 to 18 carbon atoms, and optionally comprising from 1 to 4 heteroatoms chosen from N, O, and S;

$R_a$ is chosen from:

a) a saturated or unsaturated, linear, branched, and/or cyclic carbon radicals, such as hydrocarbon (alkyl) radicals, comprising from 1 to 18 carbon atoms, and optionally comprising from 1 to 8 heteroatoms chosen from N, O, Si, and S; and b) silicone radicals of formula:

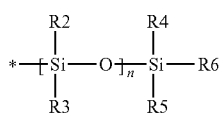

wherein:

n is a number ranging from 0 to 100, for example, from 1 to 50, from 2 to 30, or from 3 to 20; and R2 to R6, which may be identical or different, are chosen from linear or branched carbon radicals, such as hydrocarbon (alkyl) radicals, comprising from 1 to 12, for example, from 1 to 6, carbon atoms, and optionally comprising from 1 to 4 heteroatoms, such as O;

$R_b$ and $R_c$, which may be identical or different, are chosen from:

a) saturated or unsaturated, linear, branched, and/or cyclic carbon radicals, such as hydrocarbon (alkyl) radicals, comprising from 1 to 18 carbon atoms, and optionally comprising from 1 to 4 heteroatoms chosen from N, O, Si, and S;

b) radicals of formula:

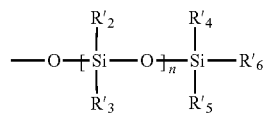

wherein:

n is a number ranging from 0 to 100, for example, from 1 to 50, from 2 to 30, or from 3 to 20; and $R'_2$ to $R'_6$, which may be identical or different, are chosen from linear or branched carbon radicals, such as hydrocarbon (alkyl) radicals, comprising from 1 to 12, for example, 1 to 6, carbon atoms, and optionally comprising from 1 to 4 heteroatoms, such as O, and ii) saturated or unsaturated, linear, branched, and/or cyclic $C_1$ to $C_{30}$ alkyl radicals optionally comprising from 1 to 3 heteroatoms chosen from O, S, F, and N; with the proviso that at least one of the radicals R and/or R' is chosen from radicals of formula (III).

The present inventors have observed that this family of bis-urea compounds may allow for the texturing of silicone media, for example, when the two radicals R and R' are silicone-based, that is to say, chosen from radicals of formula (III).

When one of the radicals R or R' is non-silicone-based, that is to say an alkyl radical as defined above, it may be possible to texture silicone media with these compounds, as well as carbon-based media and media comprising a mixture of silicone oils and carbon-based oils.

In at least one embodiment, the group A may be chosen from:

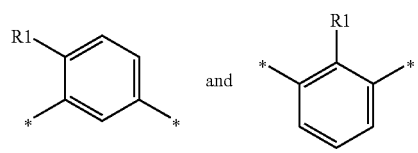

wherein $R_1$ and * are as defined above.

In one embodiment, $R_1$ may be a methyl group, such that the group A is chosen from:

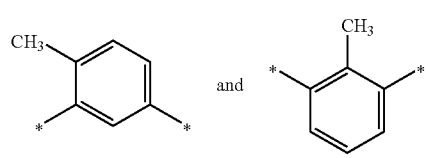

wherein * is as defined above.

In at least one embodiment, the compounds of the present disclosure may be in the form of a mixture, for instance, when A is a mixture of 2,4-tolylene and 2,6-tolylene, for example, in (2,4 isomer)/(2,6 isomer) ratios ranging from 95/5 to 80/20.

According to at least one embodiment, at least one of the radicals R and/or R' is chosen from radicals of formula (III):

(III)

In this formula, L is chosen from saturated or unsaturated, linear, branched, and/or cyclic divalent carbon radicals, such as hydrocarbon (alkylene) radicals comprising from 1 to 18 carbon atoms, and optionally comprising from 1 to 4 heteroatoms chosen from N, O, and S. In the radical L, the carbon chain may optionally be interrupted by at least one heteroatom and/or may comprise at least one substituent comprising at least one heteroatom.

In one embodiment, L may have the structure $-(CH_2)_n-$ wherein n is a number ranging from 1 to 18, for instance, from 2 to 12, or from 3 to 8. In a further embodiment, L is chosen from methylene, ethylene, propylene, butylene, for example, n-butylene, and octylene radicals.

The radical L may also be branched, for example, it may have the formula $-CH_2-CH(CH_3)-$, which leads to the following radical of formula (III):

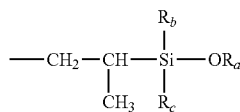

The radical $R_a$ may be chosen from saturated or unsaturated, linear, branched, and/or cyclic carbon radicals, such as hydrocarbon (alkyl) radicals, comprising from 1 to 18 carbon atoms, and optionally comprising from 1 to 8 heteroatoms chosen from N, O, Si, and S. The carbon chain may be interrupted by the at least one heteroatom and/or may comprise a substituent comprising the at least one heteroatom. In at least one embodiment; the at least one heteroatom may be in the form of an $-SiO-$ (or $-OSi-$) group.

Thus, in one embodiment, the radical $R_a$ may have the structure $-(CH_2)_{n'}-CH_3$ wherein n' is a number ranging from 0 to 17, for example, from 1 to 12, or from 1 to 6. In another embodiment, $R_a$ may be chosen from methyl, ethyl, propyl, and butyl radicals.

The radical $R_a$ may also be chosen from $-(CH_2)_x-O-(CH_2)_z-CH_3$ and $-(CH_2)_x-O-(CH_2)_y-O-(CH_2)_z-CH_3$, wherein x is a number ranging from 1 to 10, for example, 2; y is a number ranging from 1 to 10, for instance, 2, and z is a number ranging from 0 to 10, for example, 0 or 1.

The radical $R_a$ may also have the structure $-SiR_4R_5R_6$ (for example, when n=0), wherein $R_4$, $R_5$ and $R_6$, which may be identical or different, are chosen from alkyl radicals comprising from 1 to 12 carbon atoms, for instance, from 1 to 6 carbon atoms. In at least one embodiment $R_4$, $R_5$ and/or $R_6$ may be chosen from methyl, ethyl, propyl, and butyl radicals.

The radical $R_a$ may also be a silicone radical of formula:

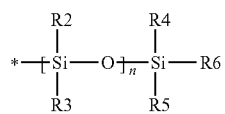

wherein R2 to R6, which may be identical or different, are chosen from alkyl radicals comprising from 1 to 12 carbon atoms, for example, from 1 to 6 carbon atoms, and n is a number ranging from 0 to 100. In at least one embodiment, R2 to R6 may be chosen from methyl, ethyl, propyl, and butyl radicals.

In another embodiment, the radial $R_a$ may be chosen from:

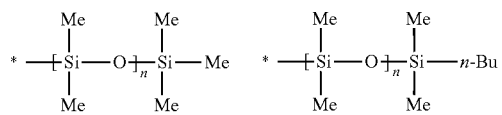

wherein n is a number ranging from 1 to 100. In a further embodiment, the radical $R_a$ has the following formula:

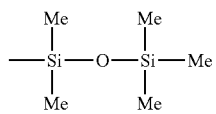

The radicals $R_b$ and $R_c$, which may be identical or different, may be saturated or unsaturated, linear, branched, and/or cyclic carbon radicals, such as hydrocarbon (alkyl) radicals, comprising from 1 to 18 carbon atoms, and optionally comprising from 1 to 8 heteroatoms chosen from N, O, Si, and S. In these radicals, the carbon chain may be interrupted by the at least one heteroatom and/or may comprise a substituent comprising the at least one heteroatom. In one embodiment, the at least one heteroatom may be in the form of an $-SiO-$ (or $-OSi-$) group.

Thus, in at least one embodiment, the radicals $R_b$ and $R_c$ may have the structure $-(CH_2)_m-CH_3$ wherein m is a number ranging from 0 to 17, for example, from 1 to 12, or from 2 to 5. In another embodiment, $R_b$ and/or $R_c$ may be chosen from methyl, ethyl, propyl, and butyl groups.

$R_b$ and $R_c$ may also be chosen from $-O-(CH_2)_{m'}-CH_3$ groups wherein m' Is a number ranging from 0 to 5, for example, from 1 to 4, such as methoxy and ethoxy groups.

In another embodiment, $R_b$ and $R_c$ may be chosen from $-O-(CH_2)_x-O-(CH_2)_z-CH_3$ and $-O-(CH_2)_x-O-(CH_2)_y-O-(CH_2)_z-CH_3$, wherein x is a number chosen from 1 to 10, for example, 2; y is a number chosen from 1 to 10, for instance, 2, and z is a number ranging from 0 to 10, for example, 0 or 1.

$R_b$ and $R_c$ may also be chosen from compounds of formula:

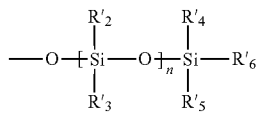

wherein n is a number ranging from 0 to 100, for instance, from 1 to 50, from 2 to 30, or from 3 to 20; and $R'_2$ to $R'_6$, which may be identical or different, are chosen from alkyl radicals comprising from 1 to 12 carbon atoms, for example, from 1 to 6 carbon atoms. In at least one embodiment, the radicals $R'_2$ to $R'_6$ may be chosen from methyl, ethyl, propyl, and butyl groups.

According to one embodiment, when they are chosen from radicals of formula (III), the radicals R and/or R' may be chosen from:

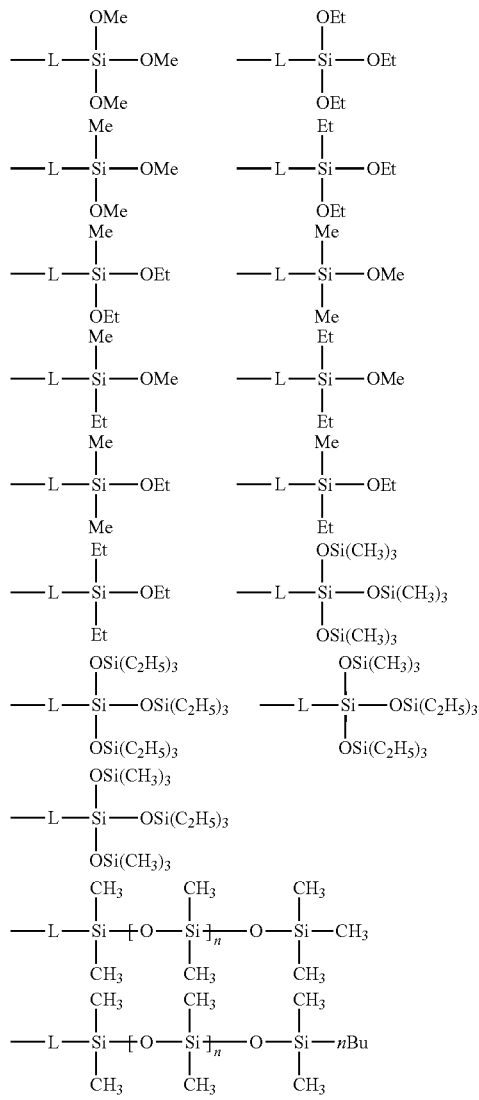

wherein n ranges from 0 to 100.

According to another embodiment, when they are chosen from radicals of formula (III), the radicals R and/or R' may be chosen from:

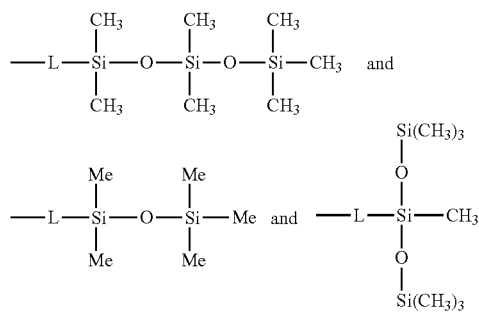

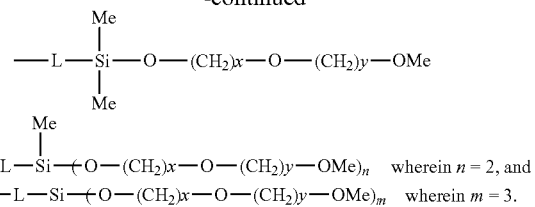

wherein x is a number ranging from 1 to 10, for instance, 2; and y is a number ranging from 1 to 10, for example, 2; and L is as defined above.

According to one embodiment, in the formulae above, L is chosen from linear or branched $C_1$-$C_8$ alkylene radicals, for example, methylene radicals, ethylene radicals, propylene radicals, butylene radicals, for instance, n-butylene radicals, octylene radicals, and radicals of formula —$CH_2$—CH($CH_3$)—.

In another embodiment, R and R', which may be identical or different, are both chosen from radicals of formula (III).

In yet another embodiment, one of the radicals R or R' is chosen from saturated or unsaturated, linear, branched, and/or cyclic $C_1$ to $C_{30}$ alkyl radicals, optionally comprising from 1 to 3 heteroatoms chosen from O, S, F, and N.

According to this embodiment, the compounds of formula (I) may have a universal character, i.e., they may be capable of texturing polar and/or a polar carbon-based media, linear or cyclic silicone media, mixed oils, i.e., carbon-based oils, partially silicone-based oils, and mixtures thereof.

The carbon chain may optionally be interrupted by the at least one heteroatom and/or may comprise a substituent comprising the at least one heteroatom, for example, carbonyl (—CO—) groups, hydroxyl (—OH) radicals, and/or of ester radicals —COOR", wherein R" is chosen from linear or branched alkyl radicals comprising from 1 to 8 carbon atoms.

Thus, in at least one embodiment, the radicals R and/or R' may be chosen from:

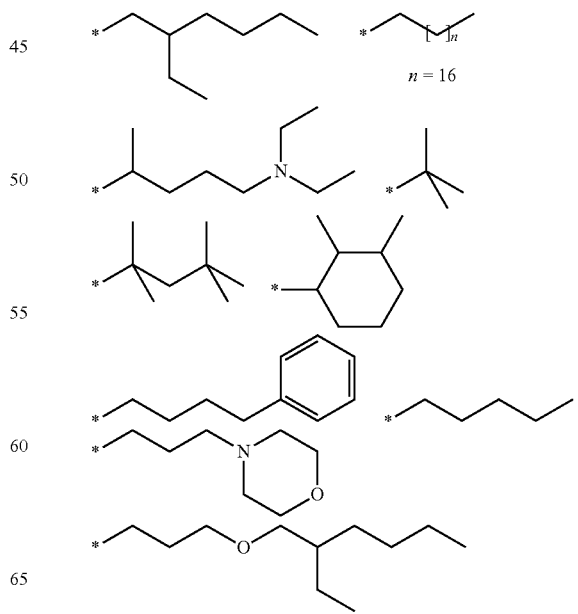

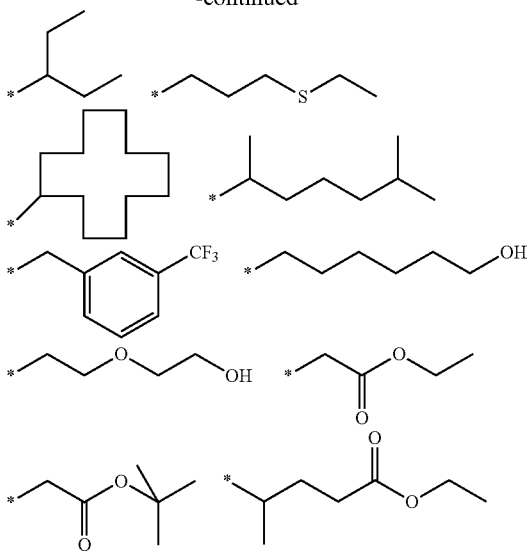

wherein * is as defined above.

In another embodiment, the radicals R and/or R' may be chosen from saturated or unsaturated, branched, for instance, monobranched, and in at least one embodiment, non-cyclic alkyl radicals comprising from 3 to 16 carbon atoms, for example, from 4 to 12, or from 4 to 8 carbon atoms, and optionally comprising from 1 to 3 heteroatoms chosen from O, S, F, and/or N, and in at least one embodiment, O and/or N. In a further embodiment, the radicals R and/or R' may be chosen from tert-butyl radicals, 2-ethylhexyl radicals, and radicals of formula:

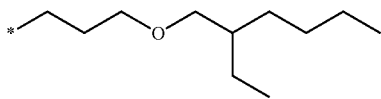

When one of the radicals R and/or R' is branched, it may allow the compound to be compatible with a broader range of solvents, for instance, silicone and carbonated solvents.

When the compound of formula (I) comprises a radical R chosen from alkyl radicals, and a radical R' which is chosen from radicals of formula (III), the ratio between $n_R$ and $n_{R'}$ may range from 5/95 to 95/5, for example from 10/90 to 90/10, from 40/60 to 85/15, from 50/50 to 80/20, or from 60/40 to 75/25;
wherein $n_R$ is the number of moles of amine $NH_2$—R and $n_{R'}$ is the number of moles of amine $NH_2$—R' used to prepare the compound of formula (I).

According to one embodiment, the compounds according to the present disclosure may also be chosen from salts and/or isomers of compounds of formula (I).

In another embodiment, the compounds according to the present disclosure may have a molecular mass lower than 5000, for example, lower than 3000, such as ranging from 300 to 5000, or from 400 to 3000, which makes it possible to differentiate them from silicone polymers, such as PDMS polymers, comprising urea functions, and which may be used, for instance, in mixtures, in gelling systems for silicone oils. Without intending to be bound by theory, it is believed that the advantage related to the use of low molecular weight molecules lies in their improved compatibility and solubility, with respect to carbonated oils and silicone oils, such as polar oils; together with their facility of being formulated, as compared to other polymers.

In at least one embodiment, the compounds of formula (I) according to the present disclosure may be chosen from the following compounds, salts thereof, isomers thereof, and mixtures thereof:

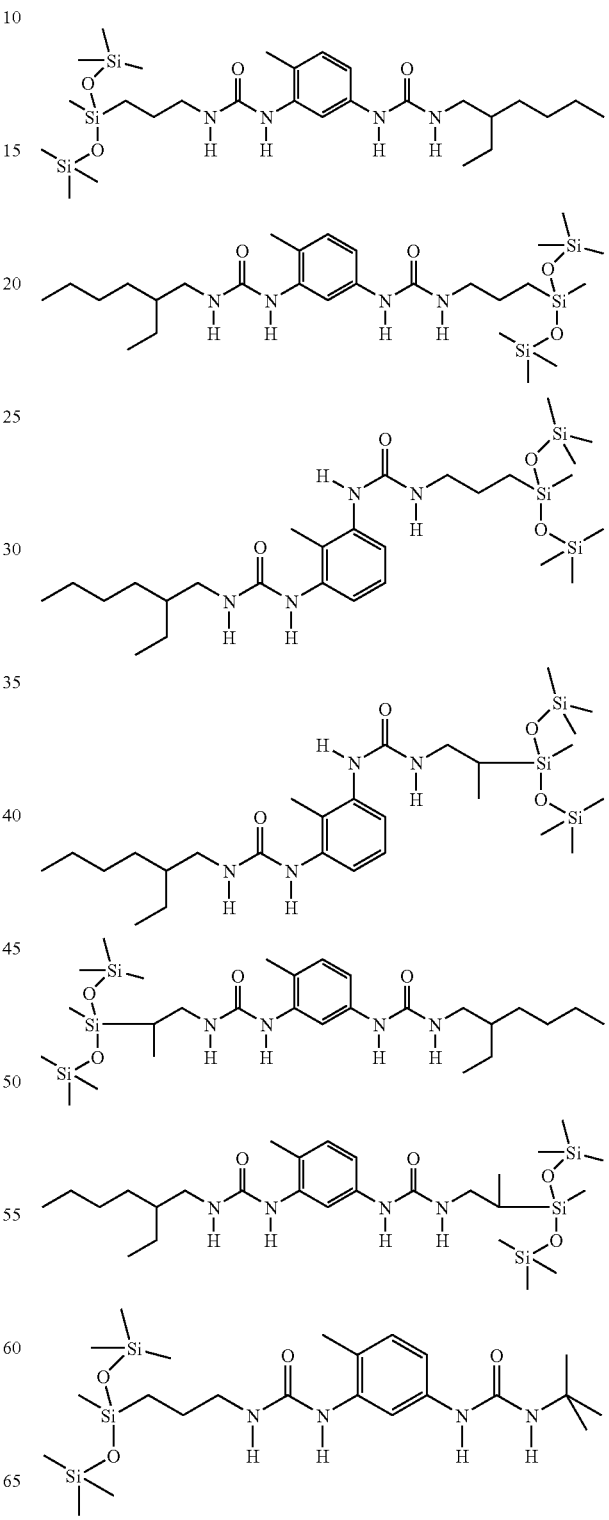

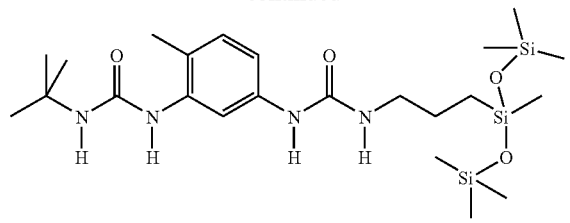
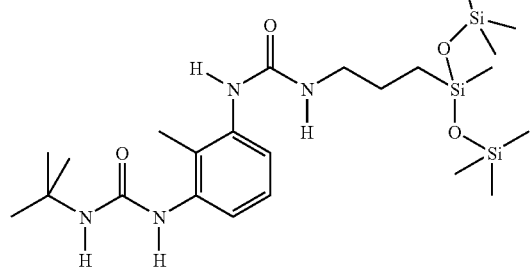
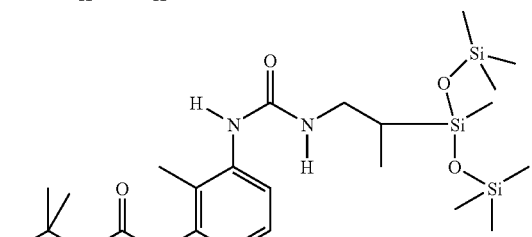
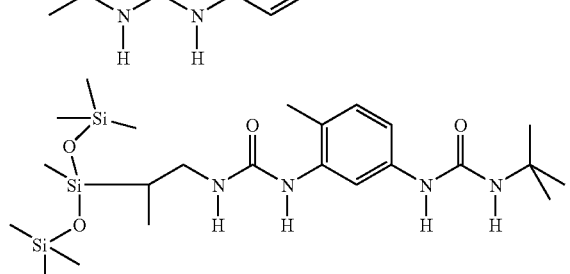
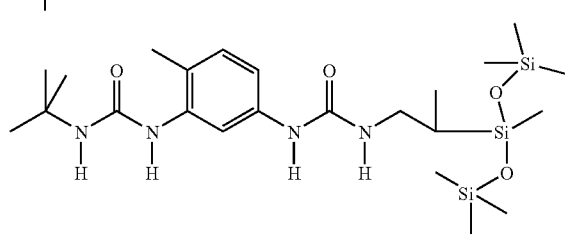
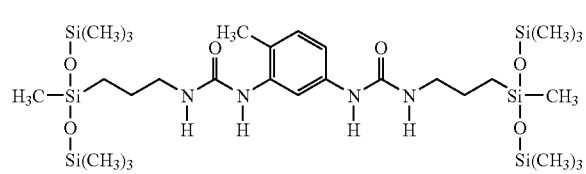
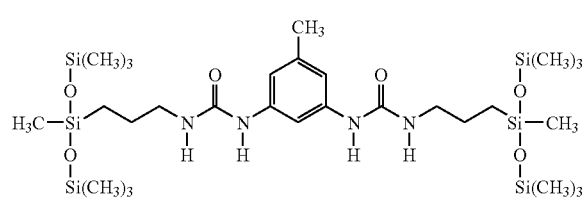

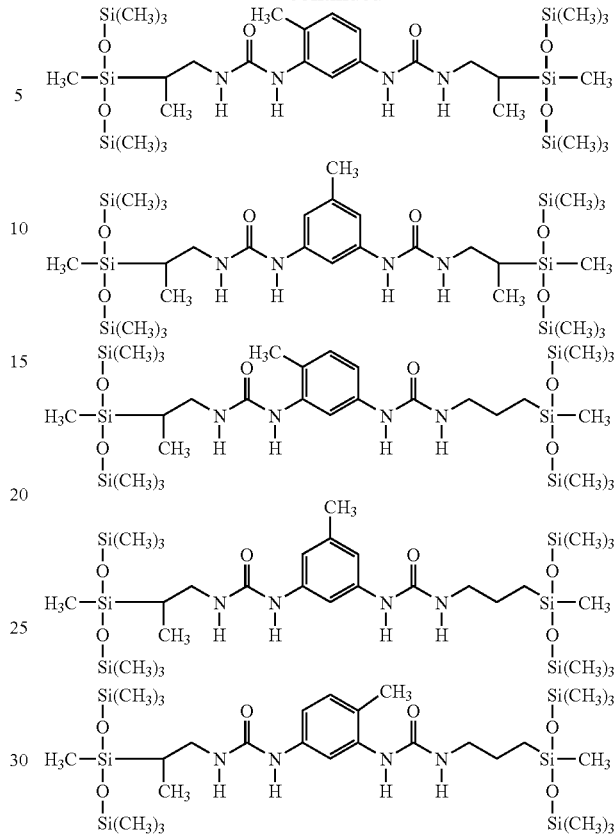

The compounds of formula (I) according to the present disclosure may be prepared by the reaction between at least one diisocyanate of formula OCN-A-NCO, and at least one primary amine R—$NH_2$, wherein A and R are defined above.

When the radicals R and R' of compound (I) are different, it may be prepared by reacting the diisocyanate with a mixture of at least two primary amines: R—$NH_2$+R'—$NH_2$.

The diisocyanate OCN-A-NCO may be provided in the form of a mixture of position isomers of the substituent $R_1$, on the group A, for example, in a ratio ranging from 95/5 to 80/20 (2,4 TDI isomer)/(2,6 TDI isomer).

In at least one embodiment, the at least one amine may be used in a molar ratio ranging from 2 to 3 equivalents, for instance, from 2.1 to 2.5, or 2.2 equivalents per equivalent of diisocyanate. The general reaction scheme is depicted below:

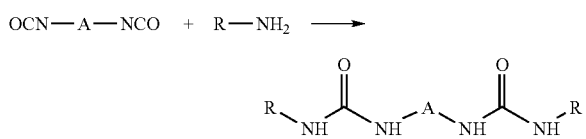

It is to be understood that it is possible to use a mixture of primary amines, for instance, two primary amines.

In the embodiment wherein two primary amines are used for the reaction, the $n_R/n_{R'}$ molar ratio may be range from 5/95 to 95/5; which may depend on the chemical nature of each of the amines, and may be determined by persons skilled in the art on the basis of their knowledge.

This molar ratio is also applicable when R and R' are both chosen from radicals of formula (III). In another embodiment, when R is an alkyl radical, and R' is a radical of formula (III), the $n_R/n_{R'}$ molar ratio may range from 5/95 to 95/5, for example, from 15/85 to 90/10, from 40/60 to 85/15, or from 50/50 to 80/20;

wherein $n_R$ is the number of moles of amine $NH_2$—R and $n_{R'}$ is the number of moles of amine $NH_2$—R' used to prepare the compound of formula (I).

A non-limiting example of a suitable mixture of primary amines is the product marketed by Clariant under the name 'aminopropylbis(trimethylsiloxy)silane', which corresponds to a mixture comprising from 80 to 99.5% by weight, for instance, from 90 to 99% by weight, of a first primary amine of formula $NH_2$—$(CH_2)_3$—$Si[OSi(CH_3)_3]_2Me$ and from 0.5 to 20% by weight, for instance, from 1 to 10% by weight of a second primary amine of formula $NH_2$—$CH_2$—$CH(CH_3)$—$Si[OSi(CH_3)_3]_2Me$.

The reaction may be generally carried out under an inert atmosphere, for example, under argon, in an anhydrous medium with, for example, a reaction medium temperature which is maintained at a value ranging from 15° C. to 40° C.

The diisocyanate may be dissolved in an anhydrous solvent such as tetrahydrofuran, 2-methyltetrahydro-furan, N-methylpyrrolidone, butyl acetate, and methyl ethyl ketone at a concentration ranging from 1 to 30% by weight, for example, from 2 to 20%, or from 4 to 10% by weight.

A solution containing the at least one amine may be prepared in the same solvent as the diisocyanate, at a concentration which may range from 0.1 to 99.9% by weight. According to one embodiment, the temperature of the reaction medium does not exceed 40° C. and the concentration of the amine as well as the rate of addition of the solution containing the amine may be adjusted accordingly.

The reaction medium may be kept stirring, for example, for 30 minutes to 12 hours. The progress of the reaction may be monitored by infrared spectrometry (e.g., by observing the disappearance of the NCO band between 2250 and 2280 $cm^{-1}$).

At the end of the reaction, the reaction medium may be poured into a large quantity of acidic water (for example, having a pH ranging from 3 to 4 with HCl). A generally white precipitate is then obtained which may be filtered, washed, for example, several times, for instance, with water, and dried under reduced pressure, such as under vacuum or freeze-dried.

The precipitate corresponds to the expected compound of formula (I), or to the expected mixture of compounds of formula (I), and may be characterized by NMR ($^1H$ and/or $^{13}C$) spectrometry and/or by mass-coupled HPLC.

The compound may be used as it is for texturing the oily medium considered.

The compounds of formula (I), and mixtures thereof in any proportions, may be solubilized in a wide variety of oils and may be effective for texturing the oils or mixture of oils considered, by conferring the desired physical and/or chemical properties on them.

In one embodiment, the compound of formula (I) may be soluble at a temperature of less than or equal to 50° C., for example, less than or equal to 30° C., or at room temperature (25° C.), in the liquid fatty phases customarily used in the cosmetics field, and therefore in the fatty phase to be textured.

Compositions

The compound according to the present disclosure may therefore be useful in customary cosmetic and/or pharmaceutical compositions, for example, as texturing agent, thickening agent, and/or gelling agent, for the liquid fatty phase contained in the compositions.

The at least one compound of formula (I) may be present in the compositions in an effective quantity, i.e., in a quantity sufficient to obtain texturing of the liquid fatty phase considered in the composition according to the present disclosure.

As used herein, the expression "textured liquid fatty phase" is understood to mean that the fatty phase assumes the state of a gel or of a thickened liquid. It can flow under its own weight. It can undergo deformation at constant volume if a stress is exerted.

This texturing may result from an increase in viscosity due, for example, to the introduction of at least one compound of formula (I).

The at least one compound of formula (I) may be present in the compositions according to the present disclosure in an amount ranging from 0.01 to 20% by weight, for example, from 0.05 to 15% by weight, from 0.1 to 10% by weight, from 1 to 8% by weight, or from 2 to 5% by weight, relative to the total weight of the composition.

The at least one compound of formula (I) may be present in the compositions according to the present disclosure in an effective amount ranging from 0.01 to 20% by weight, for example, from 0.05 to 15% by weight, from 0.1 to 10% by weight, from 1 to 8% by weight, or from 2 to 5% by weight, relative to the total weight of the at least one liquid fatty phase.

It is to be understood that the effective amount can vary, inter alia, according to the nature of the bis-urea derivative compound, whether it is used in the pure state or as a mixture with other bis-urea derivatives of formula (I), and the nature of the liquid fatty phase.

Cosmetically Acceptable Medium

The cosmetic and/or pharmaceutical compositions according to the present disclosure further comprise at least one physiologically acceptable, for instance, cosmetically acceptable, medium, i.e., a medium compatible with keratin materials such as the skin of the face and/or the body, the lips, the hair, the eyelashes, the eyebrows, the scalp, and/or the nails.

Liquid Fatty Phase

The composition according to the present disclosure comprises, in at least one physiologically acceptable medium, at least one liquid fatty phase capable of being textured.

As used herein, the expression "liquid fatty phase" is understood to mean a fatty phase that is liquid at room temperature (25° C.) and atmospheric pressure (760 mmHg), comprising at least one lipophilic compound chosen from silicone oils, carbon-based oils, and carbon-based solvents, as defined below, which are liquid at room temperature. The at least one liquid fatty phase may be present in the composition of the present disclosure in an amount ranging from 0.1 to 90% by weight of the composition, for example, from 0.5 to 35% by weight, from 1 to 30% by weight, from 2 to 20% by weight, or from 3 to 15% by weight, relative to the total weight of the composition.

Carbon-Based Oils

The liquid fatty phase may comprise at least one oil and/or solvent which may be carbon-based, such as hydrocarbon-based, and/or fluorinated. The at least one oil and/or solvent may be chosen, for example, from:

1/ esters of monocarboxylic acids with monoalcohols and polyalcohols; and in at least one embodiment, esters of the following formula: $R'_1$—CO—O—$R'_2$ wherein:

$R'_1$ is chosen from linear or branched alkyl radicals comprising from 1 to 40 carbon atoms, for instance, from 7 to 19 carbon atoms, optionally comprising at least one ethylene double bond, optionally substituted and whose hydrocarbon chain may be interrupted by at least one heteroatom chosen from N and O and/or at least one carbonyl functional group, and $R'_2$ is chosen from linear or branched alkyl radicals ranging from 1 to 40 carbon atoms, for example, from 3 to 30 carbon atoms, or from 3 to 20 carbon atoms, optionally comprising at least one ethylene double bond, optionally substituted and whose hydrocarbon chain may be interrupted by at least one heteroatom chosen from N and O and/or at least one carbonyl functional group.

As used herein, the expression "optionally substituted" is understood to mean that $R'_1$ and/or $R'_2$ may comprise at least one substituent chosen, for example, from groups comprising at least one heteroatom chosen from O and/or N, such as amino, amine, alkoxy, and hydroxyl groups.

Examples of $R'_1$ groups include, but are not limited to, those derived from higher fatty acids chosen from acetic, propionic, butyric, caproic, caprylic, pelargonic, capric, undecanoic, lauric, myristic, palmitic, stearic, isostearic, arachidic, behenic, oleic, linolenic, linoleic, oleostearic, arachidonic, and erucic acids, and mixtures thereof.

According to one embodiment, $R'_1$ may be chosen from unsubstituted branched alkyl groups comprising from 4 to 14 carbon atoms, for example, from 8 to 10 carbon atoms, and $R_2$ is chosen from unsubstituted branched alkyl groups ranging from 5 to 15 carbon atoms, for example, from 9 to 11 carbon atoms.

In another embodiment, the at least one oil and/or solvent may be chosen from $C_8$-$C_{48}$ esters, optionally comprising in their hydrocarbon chain at least one heteroatom chosen from N and O and/or at least one carbonyl functional group; for example, purcellin oil (cetostearyl octanoate); isononyl isononanoate; isopropyl myristate; 2-ethylhexyl palmitate; 2-octyldodecyl stearate; 2-octyldodecyl erucate; isostearyl isostearate; heptanoates, octanoates, decanoates, and ricinoleates of alcohols and polyalcohols, for example, fatty alcohols; and isopropyl N-lauroylsarcosinate (for example, Eldew-205SL from Ajinomoto).

2/ fluorinated oils such as perfluoropolyethers; perfluoroalkanes such as perfluorodecalin; perfluoroadamantanes; monoesters, diesters, and triesters of perfluoroalkyl phosphates; and fluorinated ester oils, 3/ hydrocarbon-based vegetable oils with a high content of triglycerides comprising fatty acid esters of glycerol in which the fatty acids may have varied chain lengths, it being possible for the latter to be saturated or unsaturated, linear or branched; for example, wheatgerm, maize, sunflower, shea, castor, sweet almond, macadamia, apricot, soybean, rapeseed, cottonseed, lucern, poppy seed, pumpkin seed, sesame, gourd, avocado, hazelnut, grape seed, blackcurrant seed, evening primrose, millet, barley, quinoa, olive, rye, safflower, candlenut, passion flower, musk rose oils, and triglycerides of caprylic/capric acids such as those sold by the company Stearinerie Dubois and those sold under the names Miglyol 810, 812, and 818 by the company Dynamit Nobel, 4/ $C_6$ to $C_{40}$ ethers, 5/ $C_8$-$C_{32}$ fatty acids, such as oleic, linoleic, and linolenic acid, 6/ "fatty" alcohols, such as $C_6$-$C_{32}$ monoalcohols such as oleyl alcohol and octyldodecanol, 7/ linear or branched hydrocarbons and fluorocarbons of synthetic or mineral origin, such as paraffin oils (such as $C_8$-$C_{16}$ isoparaffins, isododecane, and isohexadecane) and derivatives thereof, petroleum jelly, polydecenes, hydrogenated polyisobutenes such as squalane, and mixtures thereof.

Non-limiting examples of such hydrocarbons include, linear or branched, for instance, volatile, $C_6$-$C_{48}$ alkanes.

8/ bifunctional oils, comprising two functional groups chosen from esters and/or amides and comprising from 6 to 30 carbon atoms, such as from 8 to 28 carbon atoms, or from 10 to 24 carbons, and 4 heteroatoms chosen from O and N; wherein the amide and ester functional groups may be located in the chain, 9/ and mixtures thereof.

Silicone Oils

The liquid fatty phase may also comprise at least one silicone oil, which may be volatile or non-volatile. The volatile oils may have at room temperature (25° C.) and atmospheric pressure (760 mmHg) a vapor pressure ranging from 0.02 mmHg to 300 mmHg (2.66 Pa to 40 000 Pa), for example, from 0.1 to 90 mmHg (13 Pa to 12 000 Pa). The non-volatile oils may have a vapor pressure of less than 0.02 mmHg (2.66 Pa).

The at least one silicone oil may be chosen, for example, from:

linear or cyclic volatile silicone oils such as linear or cyclic polydimethylsiloxanes (PDMS) comprising from 3 to 7 silicon atoms. Non-limiting examples of such volatile oils include octyltrimethicone, hexyltrimethicone, decamethylcyclopentasiloxane (or D5), octamethylcyclotetrasiloxane (or D4), dodecamethylcyclohexasiloxane (or D6), decamethyltetrasiloxane (or L4), for instance, KF 96 A from Shin Etsu, volatile PDMSs (polydimethylsiloxane) such as DC 200 (1.5 cSt) from Dow Corning, PDMS DC 200 (2 cSt) from Dow Corning, PDMS DC 200 (5 cSt) from Dow Corning, and PDMS DC 200 (3 cSt) from Dow Corning, and mixtures thereof.

Further examples include, but are not limited to, heptamethyloctyltrisiloxane, dodecamethylpentasiloxane, polymethylcetyldimethylsiloxane, and mixtures thereof.

The volatile silicone oil may also be chosen, by way of non-limiting example, from fluorinated silicone oils such as silicones comprising alkyl and perfluoroalkyl groups, silicones comprising oxyethylenated/oxypropylenated (OE/PP) side groups and comprising perfluorinated groups, silicones comprising perfluorinated or polyfluorinated side groups and comprising glycerolated side groups, and perfluoroalkylmethylphenylsiloxanes.

non-volatile silicone oils such as polydimethylsiloxanes (PDMS), polyalkylmethylsiloxanes, dimethicone copolyols, alkylmethicone copolyols, cetyldimethicone, silicones comprising alkylglyceryl ether groups, silicones comprising amine side groups, and dilauroyltrimethylol propane siloxysilicate. The alkyl groups of these oils may comprise, for example, from 2 to 24 carbon atoms.

The non-volatile silicone oils may be chosen, for instance, from non-volatile polydimethylsiloxanes (PDMS) which are liquid at room temperature; the polydimethylsiloxanes comprising alkyl, alkoxy, and/or phenyl groups which are pendant and/or at the silicone chain end, groups comprising from 2 to 24 carbon atoms; phenylated silicones such as phenyl trimethicones, phenyl dimethicones, phenyl trimethylsiloxy diphenylsiloxanes, diphenyl dimethicones, diphenyl methyldiphenyl trisiloxanes, 2-phenylethyl trimethylsiloxysilicates, cetyldimethicone, silicones comprising alkylglyceryl ether groups, silicones comprising amine side groups, fluorinated silicones comprising at least one pendant group or at least one groups at the chain end comprising from 1 to 12 carbon atoms in which all or part of the hydrogen atoms are substituted with fluorine atoms, dimethiconols, and/or mixtures thereof.

and mixtures thereof.

The liquid fatty phase to be textured may comprise a mixture of carbon-based and silicone oils which may be textured by the compounds of formula (I) according to the present disclosure.

In at least one embodiment, the compositions according to the present disclosure comprise a liquid fatty phase which comprises at least one lipophilic compound chosen from:

$C_6$-$C_{32}$, for example, $C_8$-$C_{28}$, such as $C_{12}$-$C_{26}$, monoalcohols, for instance, octyldodecanol;

$C_6$-$C_{32}$, for example, $C_8$-$C_{28}$, such as $C_{12}$-$C_{26}$, branched alkanes, for instance, isododecane and parleams of formula —$(CH_2$—$CH(CH_3))_n$—, wherein n is an integer ranging from 4 to 8;

$C_{13}$-$C_{48}$, for example, $C_{18}$-$C_{40}$, such as $C_{20}$-$C_{32}$, linear alkanes;

bifunctional oils, comprising two functional groups chosen from esters and/or amides and comprising from 6 to 30 carbon atoms, for example, 8 to 28 carbon atoms, or from 10 to 24 carbon atoms, and 4 heteroatoms chosen from O and N; wherein the amide and ester functional groups may optionally be located in the chain; for instance, the bifunctional oil may be the isopropyl N-lauroylsarcosinate of the following formula:

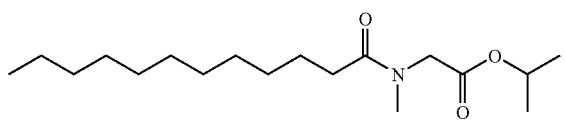

which is sold, for example, under the name Eldew SL-2050 from Ajinomoto;

$C_8$-$C_{48}$ esters, optionally comprising in their hydrocarbon chain at least one heteroatom from N and O and/or at least one carbonyl functional group; for example, purcellin oil (cetostearyl octanoate); isononyl isononanoate; isopropyl myristate; 2-ethylhexyl palmitate; 2-octyldodecyl stearate; 2-octyldodecyl erucate; isostearyl isostearate; and heptanoates, octanoates, decanoates, and ricinoleates of alcohols and polyalcohols, for example, of fatty alcohols;

volatile or non-volatile silicone oils, such as linear or cyclic polydimethylsiloxanes (PDMS) comprising from 3 to 7 silicon atoms such as decamethylcyclopentasiloxane, octamethylcyclotetrasiloxane, dodecamethylcyclohexasiloxane, decamethyltetrasiloxane; and phenylated silicones such as phenyl trimethicones;

and mixtures thereof.

These lipophilic compounds may be present in the composition in an amount ranging from 20 to 100%, for instance, from 40 to 99%, or from 60 to 95% by weight relative to the total weight of the liquid fatty phase.

Combinations of at least one bis-urea type compound of formula (I) with at least one lipophilic compound as defined may give satisfactory results in the compositions of the present disclosure.

Solid Fatty Substances

The compositions according to the present disclosure may further comprise at least one solid fatty substance which may be chosen from waxes and/or pasty compounds. The at least one solid fatty substance may be present in the compositions according to the present disclosure in an amount ranging from 0.1% to 40% by weight, for example, from 0.1% to 30% by weight, or from 0.5% to 25% by weight of solid fatty substances relative to the total weight of the composition.

Non-limiting examples of pasty fatty substances include silicone gums.

As used herein, the expression "wax" is understood to mean a lipophilic compound which is solid at room temperature (25° C.) and which has a reversible solid/liquid change of state, and which has a melting point greater than or equal to 30° C., for example, greater than 45° C., and which may range up to 120° C. The waxes may be chosen from plant, animal, mineral, and synthetic oils; they may be carbon-based, for instance, hydrocarbon-based, fluorinated, and/or silicone-based. Examples of such waxes include, but are not limited to, beeswax, carnauba wax, Candelilla wax, paraffin, microcrystalline waxes, ceresin, ozokerite; synthetic waxes such as polyethylene andor Fischer-Tropsch waxes, silicone waxes, such as alkyldimethicones and alkoxydimethicones comprising from 16 to 45 carbon atoms; and mixtures thereof.

Aqueous Phase

The composition may further comprise an aqueous phase which may comprise water or a mixture of water and at least one water-miscible organic solvent, chosen, for example, from monoalcohols comprising from 1 to 5 carbon atoms, such as ethanol and isopropanol; glycols comprising from 2 to 8 carbon atoms, such as propylene glycol, ethylene glycol, 1,3-butylene glycol, and dipropylene glycol; $C_3$-$C_4$ ketones; and $C_2$-$C_4$ aldehydes.

The aqueous phase may be present in the composition in an amount ranging from 1% to 95% by weight, for example, from 3% to 80% by weight, or from 5% to 60% by weight, relative to the total weight of the composition.

In another embodiment, the composition of the present disclosure may be free of water (0%).

Colorants

The composition according to the present disclosure may further comprise at least one organic or inorganic colorant, which may be chosen from lipophilic dyes, hydrophilic dyes, pigments, pearlescent agents, materials having a specific optical effect, and mixtures thereof. The at least one colorant may be present in the composition in an amount ranging from 0.01 to 50% by weight relative to the total weight of the composition, for example, from 0.5 to 40%, from 1 to 25%, or from 5 to 20% by weight relative to the total weight of the composition.

Fillers

The composition according to the present disclosure may further comprise at least one filler, such as in an amount ranging from 0.01% to 50% by weight, relative to the total weight of the composition, for example, from 0.05% to 30% by weight.

Additives

The composition according to the present disclosure may also comprise at least one optional additive commonly used in the cosmetics field, such as vitamins, thickeners, gelling agents, trace elements, emollients, sequestrants, perfumes, alkalifying or acidifying agents, preservatives, sunscreens, surfactants, antioxidants, antihair-loss agents, antidandruff agents, propellants, ceramides, polymers, cosmetic active agents, and mixtures thereof. It is to be understood that a person skilled in the art will be careful to choose the at least one optional additional compound, and/or its quantity, such that the advantageous properties of the composition according to the present disclosure are not, or not substantially, impaired by the addition envisaged.

The composition according to the present disclosure may be provided in a form chosen from suspensions, dispersions, solutions, which may be organic, gels, emulsions, such as oil-in-water (O/W), water-in-oil (W/O), and multiple (e.g., W/O/W, polyol/O/W, and O/W/O) emulsions, creams, pastes, mousses, dispersions of vesicles, such as dispersions of ionic or non-ionic lipids, two-phase lotions, multiphase lotions, sprays, powders, sticks, and batons.

It is to be understood that persons skilled in the art will be able to choose the appropriate galenic form, and its method of preparation, on the basis of their general knowledge, taking into account the nature of the constituents used, such as their solubility in the carrier, and the application envisaged for the composition.

The composition according to the present disclosure may be a make-up composition, for instance, products for the complexion such as foundations, blushers, and eye shadows; products for the lips such as lipsticks and care products for the lips; concealer products; blushers; mascaras; eyeliners; make-up products for the eyebrows; lip pencils; eye pencils; products for the nails such as nail varnishes and care products for the nails; and make-up products for the body and/or the hair (e.g., mascaras and lacquers for the hair).

The composition according to the present disclosure may be a composition for protecting and/or caring for the skin of the face, the neck, the hands, and/or the body, such as anti-wrinkle, anti-fatigue, and anti-ageing compositions, which may make it possible to make the skin radiant, moisturizing and/or treatment compositions; and anti-sun, after-sun, and/or artificial tanning compositions.

The composition according to the present disclosure may also be a hair product, for example a product for hair dyeing, care and hygiene, hair-styling, holding the hairstyle, and/or shaping the hair. The hair compositions may be chosen from shampoos, gels, hair setting lotions, blow drying lotions, hair care and/or hygiene compositions, and/or fixing and hair-styling compositions, such as lacquers, gels, and sprays.

According to at least one embodiment, the composition according to the present disclosure is a make-up composition, for example, foundations, mascaras, and lipsticks.

The composition according to the present disclosure may be manufactured by known processes, generally used in the cosmetics and/or pharmaceutical fields.

Methods

Also disclosed herein is a method of cosmetic treatment, such as a method for making-up, cleansing, sun protection, shaping, dyeing, and/or caring for keratin materials, for example, the skin of the body and/or the face, the lips, the nails, the eyebrows, the hair, and/or the eyelashes, comprising applying to the materials at least one cosmetic composition of the present disclosure.

Further disclosed herein is a method for texturing a cosmetic and/or pharmaceutical composition comprising adding to the composition at least one compound of formula (I) of the present disclosure.

Other than in the examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the disclosure are approximations, unless otherwise indicated the numerical values set forth in the specific examples are reported as precisely as possible. Any numerical value, however, inherently contains certain errors necessarily resulting from the standard deviation found in their respective testing measurements.

By way of non-limiting illustration, concrete examples of certain embodiments of the present disclosure are given below.

EXAMPLES

General Method of Preparation

Various preparations of bis-urea type compounds were made, comprising at least one silicone unit and at least one non-silicone unit. The various mixtures were obtained in one step, according to the general synthesis scheme below:

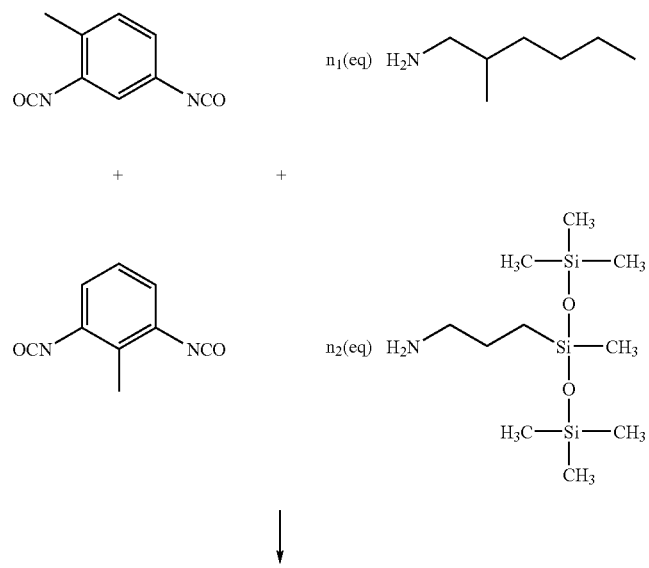

-continued

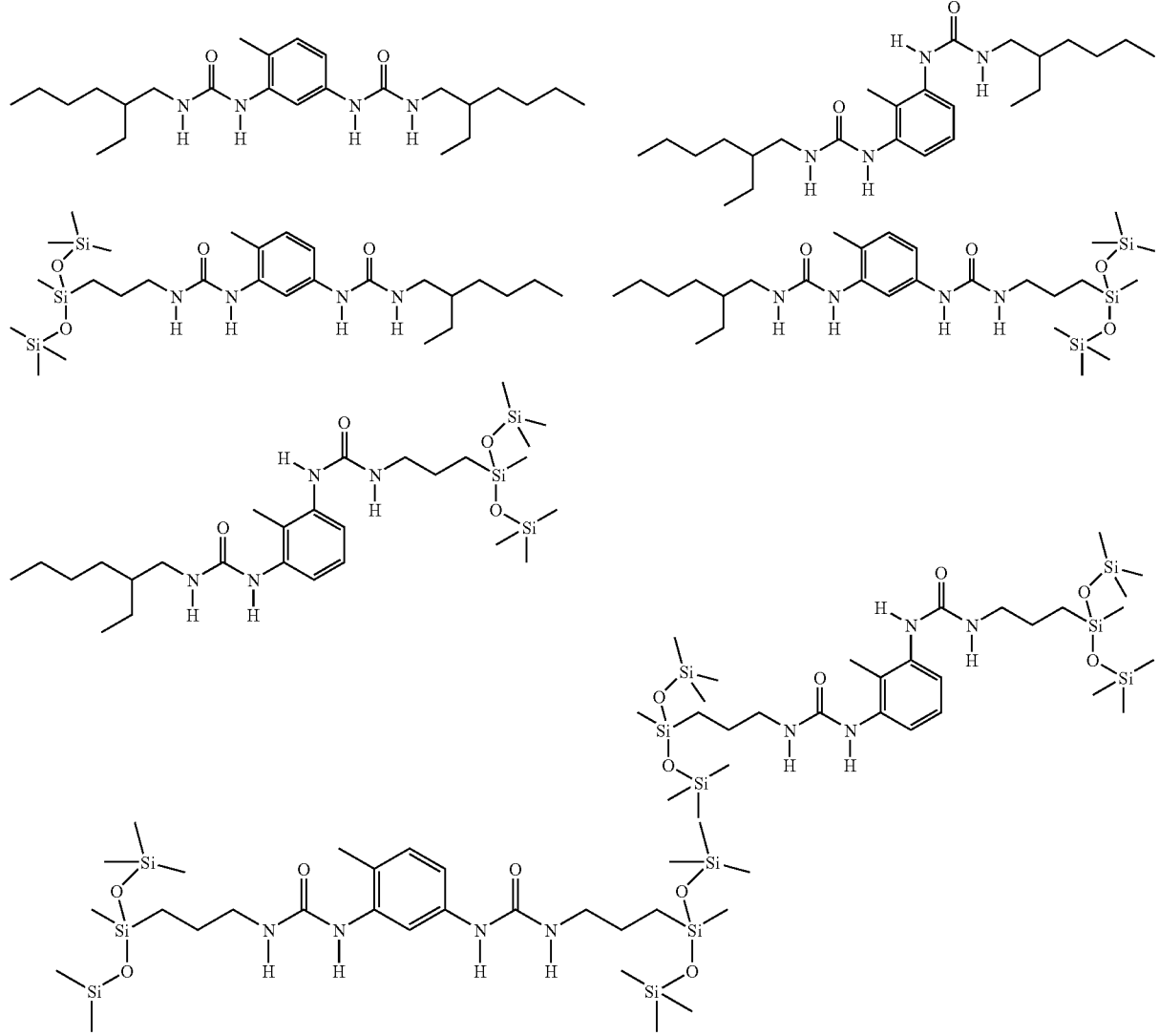

Various mixtures were prepared according to the ratio of $n_1$ (number of moles of 2-ethylhexylamine) over $n_2$ (number of moles of 3-aminopropylmethylbis(trimethylsiloxy)silane) and the percentage of toluene diisocyanate (TDI) isomer (95/5 or 80/20).

These mixtures were prepared according to the same procedure as described below. The specific quantities selected for each starting raw material are specified in the examples below.

Tolylene diisocyanate dissolved in anhydrous THF was mixed with 2.2 equivalents of amine dissolved in anhydrous THF.

The reaction was carried out under an inert atmosphere (argon) in anhydrous medium with a temperature of the reaction medium which was maintained at a value ranging from 15° C. to 40° C.

In parallel, a solution of amine (Y) was prepared in THF. Since the temperature of the reaction medium generally should not exceed 40° C., the amine concentration and the rate of addition of the amine solution (Y) were adjusted accordingly. The reaction medium was kept stirred while monitoring the progress of the reaction by infrared spectrometry (disappearance of the NCO band between 2250 and 2280 $cm^{-1}$).

Once the diisocyanate had completely reacted, the reaction mixture was added to acidified water (pH 3) with hydrochloric acid, the precipitate obtained was filtered, washed several times with water, and finally dried under vacuum or freeze-dried. A white powder was obtained and used as-is after analysis (mass-coupled HPLC).

Examples 1 and 2

(R=R'=3-aminopropylmethylbis(trimethylsiloxy) silane)

In these examples, the mixture finally obtained was characterized by mass-coupled HPLC and by $^1$H NMR.

Example 1

Starting raw materials:
TDI: 95/5 as (2,4 isomer)/(2,6 isomer); m=5 g (28.71 mmol)
$n_1$=0
$n_2$=63.16 mmol (2.2 eq.) that is m=17.6 g of 3-aminopropylmethylbis(trimethylsiloxy)silane, with a beta isomer level of less than 1%.

Example 2

Starting raw materials:
TDI: 80/20 as (2,4 isomer)/(2,6 isomer)
$n_1=0$
$n_2=63.16$ mmol (2.2 eq.) that is m=17.6 g of 3-aminopropylmethylbis(trimethylsiloxy)silane, with a beta isomer level of less than 1%.

The mixture finally obtained in Examples 1 and 2 comprised the following bis-ureas:

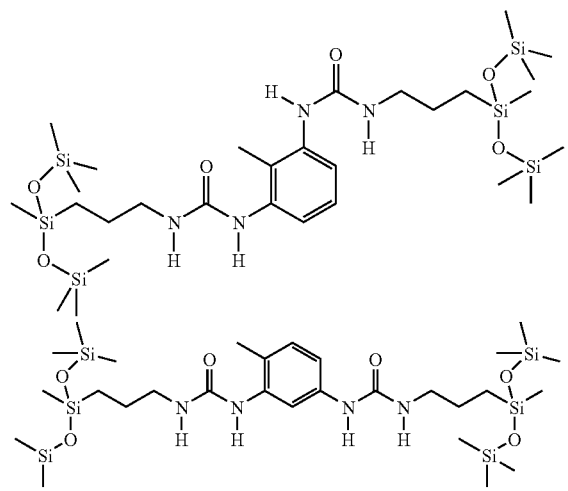

Examples 3 and 4

(R=2-ethylhexyl and R'=3-aminopropylmethylbis(trimethylsiloxy)silane)

In these examples, the mixture finally obtained was characterized by mass-coupled HPLC and $^1$H NMR.

Example 3

Starting raw materials:
TDI: 95/5 as (2,4 isomer)/(2,6 isomer); m=0.317 g (1.82 mmol)
$n_1=2$ mmol (1.1 eq.) that is m=0.259 g of 2-ethylhexylamine;
$n_2=2$ mmol (1.1 eq.) that is m=0.560 g of 3-aminopropylmethylbis(trimethylsiloxy)silane, with a beta isomer level of less than 1%.
Therefore $n_R/n'_R=1$.

Example 4

Starting raw materials:
TDI: 95/5 as (2,4 isomer)/(2,6 isomer); m=50 g (0.29 mol)
$n_1=0.44$ mol (1.5 eq.) that is m=56.87 g of 2-ethylhexylamine;
$n_2=0.19$ mol (0.66 eq.) that is m=53.13 g of 3-aminopropylmethylbis(trimethylsiloxy)silane, with a beta isomer level of less than 1%. Therefore $n_R/n'_R=2.23$ (69/31).

The mixture finally obtained in Examples 3 and 4 comprised the following bis-ureas:

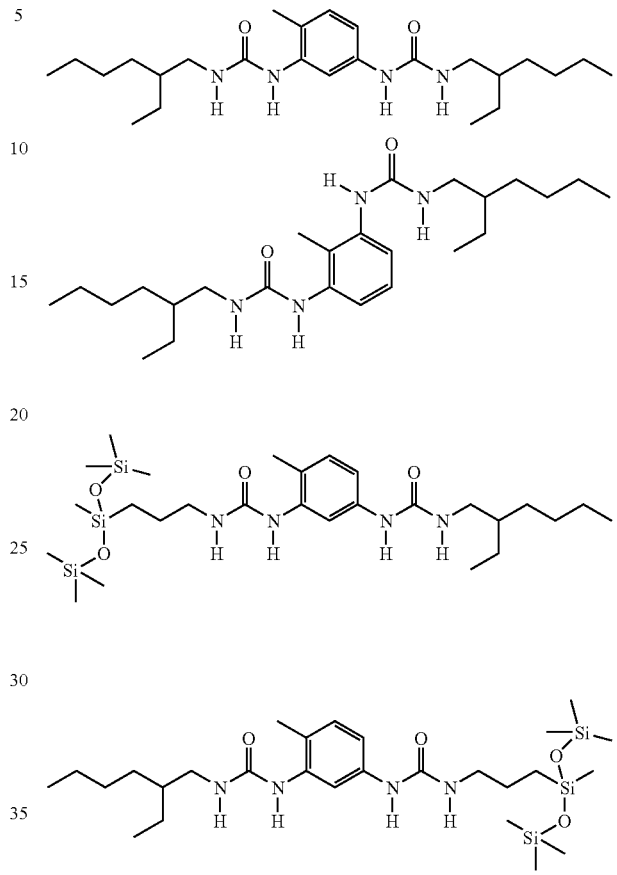

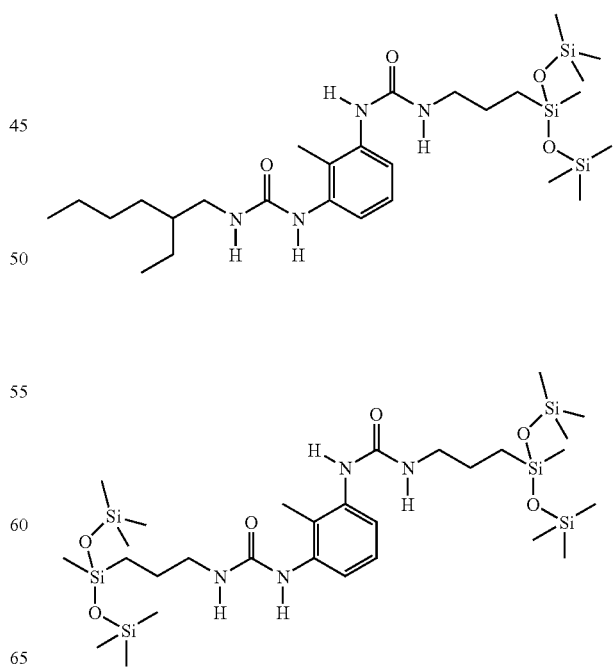

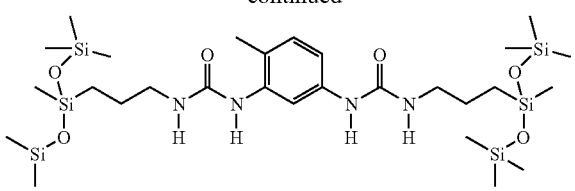

The molecular weight of the compounds having one silicone moiety was 582, and the molecular weight of compounds having two silicone moieties (one on each side) was 732.

Example 5

The mixtures prepared in Examples 1 to 4 above, and comparative compounds A and B, were tested in an amount of 1% by weight in 100 ml of various lipophilic compounds, for their thickening and/or texturing properties, at room temperature (25° C., 1 atm.).

The lipophilic compounds chosen were: isododecane, parleam, octyldodecanol, isononyl isononanoate, phenyl trimethicone, volatile silicone D5, and volatile silicone L4.

The thickening/texturing properties were judged satisfactory if the mixture of compounds was solubilized at room temperature in the said lipophilic compound, and if an increase in the viscosity of the said lipophilic compound was observed. The color and homogeneity of the solutions obtained were also evaluated.

The comparative mixtures A and B were the following:
Comparative A:
starting raw materials:
  TDI: 95/5 as (2,4 isomer)/(2,6 isomer)
  $n_1$=2.2 eq. (2-ethylhexylamine) and $n_2$=0
Comparative B:
starting raw materials:
  TDI: 95/5 as (2,4 isomer)/(2,6 isomer)
  $n_1$=1.6 eq. of 2-ethylhexylamine
  $n_2$=0
  n3=0.4 eq. of tert-butylamine
The results of the tests are illustrated in the tables below:

|  | Phenyltrimethicone | D5 | L4 |
|---|---|---|---|
| Example 1 | White homogeneous medium Increase in the viscosity | Clear homogeneous medium Increase in the viscosity | Clear homogeneous medium Increase in the viscosity |
| Example 2 | White medium + deposit Increase in the viscosity | White medium Increase in the viscosity | Phase separation Increase in the viscosity |
| Example 3 | Insoluble | Clear medium Increase in the viscosity | Not tested |
| Example 4 | Clear medium Increase in the viscosity | Clear medium Increase in the viscosity | Clear medium Increase in the viscosity |
| Comparative A | Insoluble | Insoluble (even after heating to 80° C.) | Insoluble |
| Comparative B | Clear medium Increase in the viscosity | Insoluble | Insoluble |

|  | Isododecane | Parleam | Octyl-dodecanol | Isononyl isonanoate |
|---|---|---|---|---|
| Example 1 | Clear medium but phase separation over time Increase in the viscosity | White medium Increase in the viscosity | Translucent medium but deposit Increase in the viscosity | Opaque medium with phase separation Increase in the viscosity |
| Example 2 | Phase separation, Increase in the viscosity | Clear homogeneous medium Increase in the viscosity | Light white film No increase in the viscosity | Opaque medium with deposit Increase in the viscosity |
| Example 3 | Clear medium Increase in the viscosity | Insoluble | Insoluble | Insoluble |
| Example 4 | Clear medium Increase in the viscosity | Clear medium Increase in the viscosity | Clear medium Increase in the viscosity | Clear medium Increase in the viscosity |
| Comparative A | Clear medium Increase in the viscosity | Clear medium Increase in the viscosity | Clear medium Increase in the viscosity | Deposit Increase in the viscosity |
| Comparative B | Clear medium Increase in the viscosity | Clear medium Increase in the viscosity | Clear medium Increase in the viscosity | Clear medium Increase in the viscosity |

It was observed that the compounds of Examples 1 to 4, in accordance with the present disclosure, made it possible to gel a wide range of silicone solvents (partially silicone-based such as phenyltrimethicone, purely silicone-based and cyclic such as D5 and, purely silicone-based and linear such as L4) and to give clear and homogeneous solutions in most cases.

Moreover, the compounds of Examples 3 and 4 according to the present disclosure, in which a radical R is carbon-based (alkyl), made it possible to texture/thicken a wide range of silicone solvents (linear and cyclic), but also polar or a polar carbon-based oils and solvents, while giving clear and homogeneous solutions in most cases.

This was, however, not the case with the compounds of Examples 1 and 2, which are purely silicone-based; these compounds made it possible to texture/thicken the carbon-based oils envisaged, but the solutions obtained were not always clear, sometimes exhibiting deposits or phase separation.

Example 6

In a manner similar to that described in Example 1, the following compound was prepared:
Starting raw materials:
TDI: 95/5 as (2,4 isomer)/(2,6 isomer); m=10 g (57.41 mmol)
$n_1=0$
$n_2=126.3$ mmol (2.2 eq.) that is m=35.23 g of 3-aminopropylmethylbis(trimethylsiloxy)silane, with a beta isomer level of less than 10% (assayed at 7%); that is to say a mixture of amine of formula $NH_2—CH_2—CH_2—CH_2—Si[OSi(CH_3)_3]_2Me$ and of amine of formula: $NH_2—CH_2—CH(CH_3)—Si[OSi(CH_3)_3]_2Me$ (called beta isomer), the second being present in a quantity of less than 10% by weight.

The mixture finally obtained behaved like that of Example 1, which contained a maximum of 1% by weight of beta isomer: it is solubilized and increased the viscosity of silicone oils, such as D5 and L4.

Example 7

In a manner similar to that described in Example 1, the following compound was prepared:
Starting raw materials:
TDI: 95/5 as (2,4 isomer)/(2,6 isomer)
$n_1=0$
$n_2=2.2$ eq. of bis-trimethylsilanylmethylamine (primary amine containing silicon).

The mixture obtained was insoluble in all the solvents mentioned in Example 5. This example shows that it is not sufficient to add a silicon unit to the structure of the organogelling compound to obtain a compound capable of gelling silicone-based and/or carbon-based solvents, and even less both carbon-based and silicone-based solvents.

Example 8

Hair-Styling Gel

A hair-styling gel composition was prepared comprising (% by weight):

| | |
|---|---|
| compound of Example 4 | 3% |
| isoeicosane | 5% |

-continued

| | |
|---|---|
| tridecyl trimellitate | 5% |
| isododecane | qs 100% |

A very thick, crystal gel was obtained which was a haircare product with satisfactory qualities.

Example 9

Make-Up Foundation

A make-up foundation was prepared comprising (% by weight):

| | |
|---|---|
| Compound of Example 1 | 1.5% |
| Cyclopentasiloxane | 65% |
| titanium dioxide | 7% |
| Glycerin | 3% |
| Nylon-12 | 2.5% |
| iron Oxides | 2.5% |
| bis-PEG/PPG-14/14 dimethicone | 1.8% |
| magnesium sulfate | 0.7% |
| Isostearyl diglyceryl succinate | 0.6% |
| preservatives | qs |
| Water | qsp 100% |

What is claimed is:

1. A cosmetic and/or pharmaceutical composition comprising, in a physiologically acceptable medium, at least one fatty phase and at least one compound chosen from the following compounds, salts thereof, isomers thereof, and mixtures thereof:

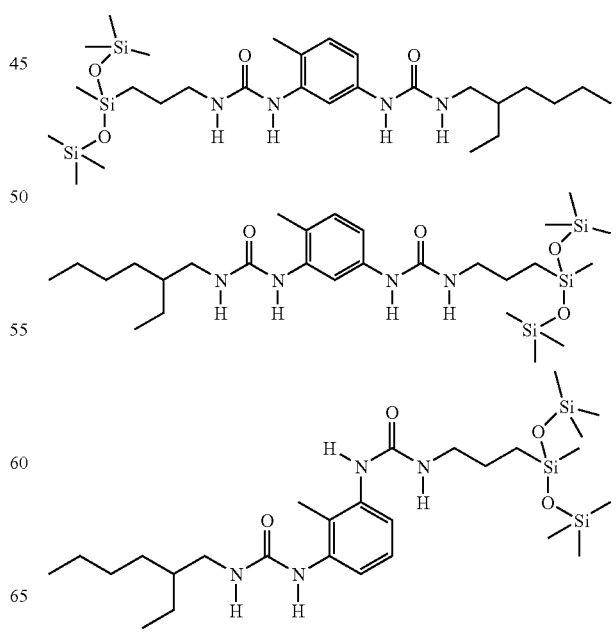

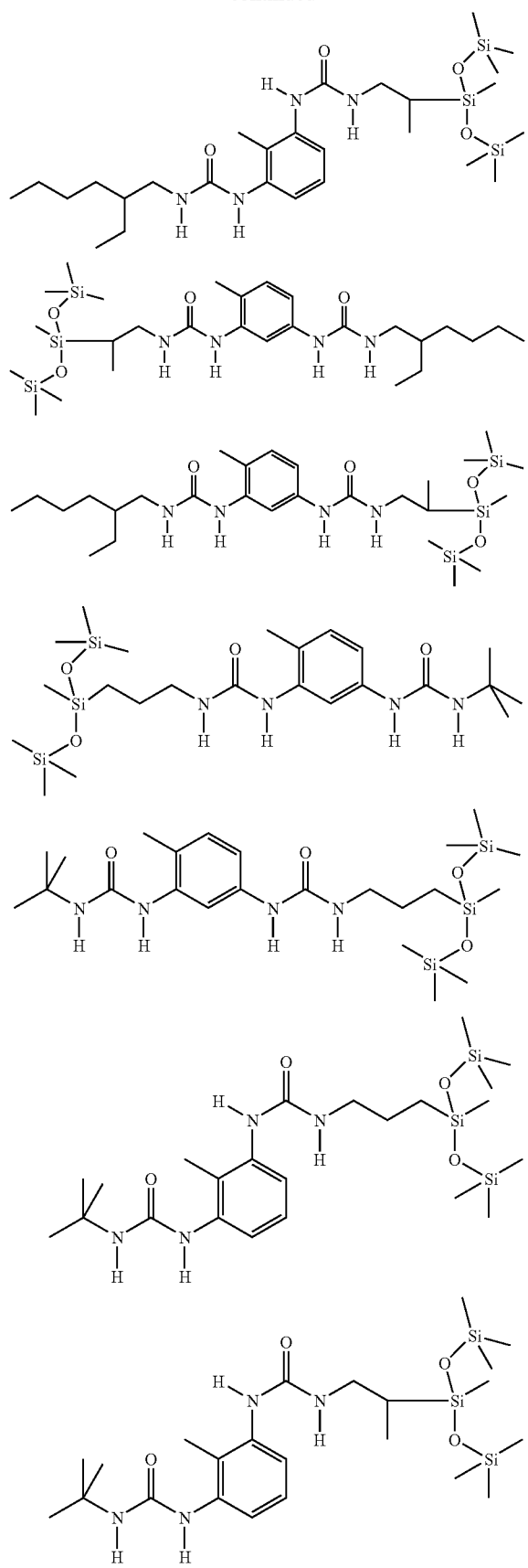
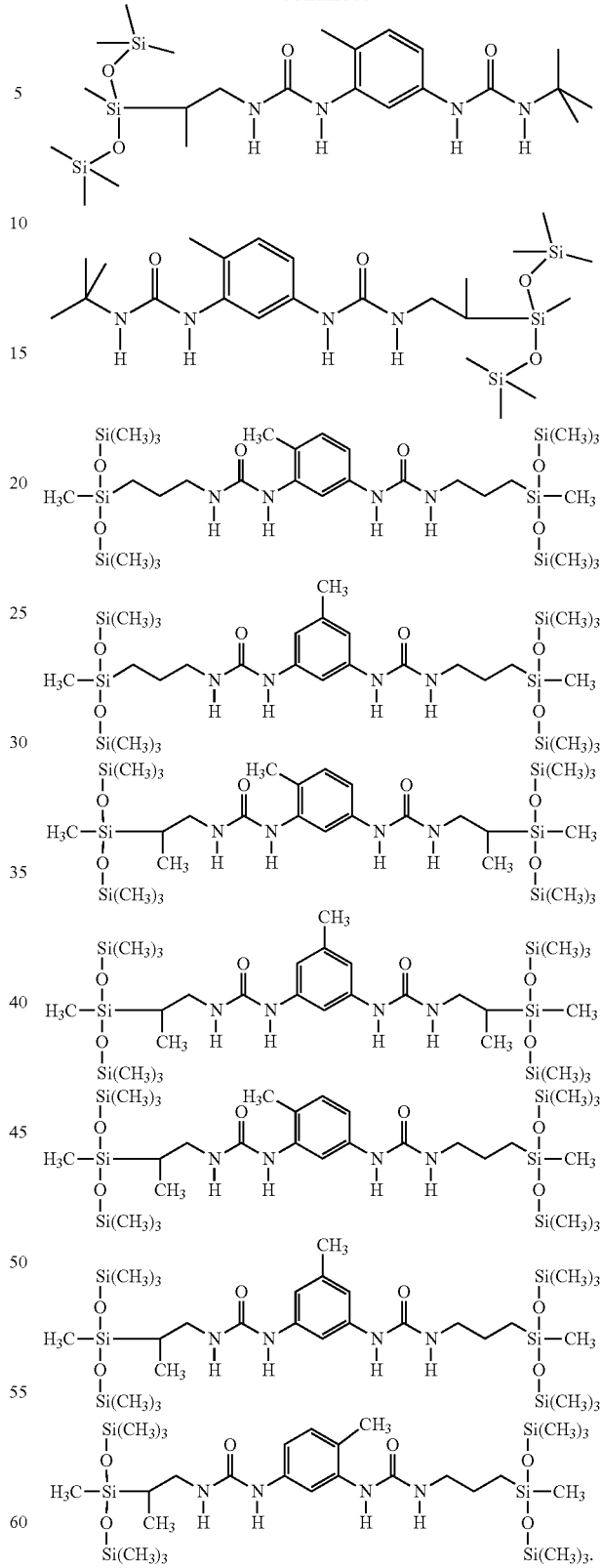
2. The composition of claim 1, wherein the at least one compound is present in the composition in an amount ranging from 0.01 to 20% by weight relative to the total weight of the composition.

3. The composition of claim 2, wherein the at least one compound is present in the composition in an amount ranging from 0.1 to 10% by weight relative to the total weight of the composition.

4. The composition of claim 3, wherein the at least one compound is present in the composition in an amount ranging from 2 to 5% by weight relative to the total weight of the composition.

5. The composition of claim 1, wherein the at least one liquid fatty phase comprises at least one lipophilic compound chosen from silicone oils, carbon-based oils, and carbon-based solvents, which are liquid at room temperature.

6. The composition of claim 1, wherein the at least one liquid fatty phase comprises at least one lipophilic compound chosen from:
   a. esters of monocarboxylic acids with monoalcohols and polyalcohols;
   b. fluorinated oils;
   c. hydrocarbon-based vegetable oils with a high content of triglycerides comprising fatty acid esters of glycerol in which the fatty acids may have varied chain lengths, it being possible for the latter to be saturated or unsaturated, linear or branched;
   d. $C_6$ to $C_{40}$ ethers,
   e. $C_8$-$C_{32}$ fatty acids,
   f. fatty alcohols;
   g. linear or branched hydrocarbons and fluorocarbons of synthetic or mineral origin;
   h. bifunctional oils, comprising two functional groups chosen from esters and/or amides and comprising from 6 to 30 carbon atoms and 4 heteroatoms chosen from O and N;
   i. linear or cyclic, optionally fluorinated, volatile or non-volatile silicone oils; and mixtures thereof.

7. The composition of claim 6, wherein:
   the esters of monocarboxylic acids with monoalcohols and polyalcohols are chosen from compounds of formula $R'_1$—CO—O—$R'_2$ wherein:
   $R'_1$ is chosen from linear or branched alkyl radicals comprising from 1 to 40 carbon atoms, optionally comprising at least one ethylene double bond, optionally substituted, and whose hydrocarbon chain may be interrupted by at least one heteroatom chosen from N and O and/or at least one carbonyl functional group, and
   $R'_2$ is chosen from linear or branched alkyl radicals comprising from 1 to 40 carbon atoms, optionally comprising at least one ethylene double bond, optionally substituted, and whose hydrocarbon chain may be interrupted by at least one heteroatom chosen from N and O and/or at least one carbonyl functional group; and/or
   the fatty alcohols are chosen from $C_6$-$C_{32}$ monoalcohols; and/or
   the bifunctional oils comprise in their chain at least one group chosen from esters and/or amides.

8. The composition of claim 1, wherein the at least one liquid fatty phase comprises at least one lipophilic compound chosen from:
   $C_8$-$C_{48}$ esters, optionally comprising in their hydrocarbon chain at least one heteroatom chosen from N and O and/or at least one carbonyl functional group;
   perfluoropolyethers; perfluoroalkanes; perfluorodamantanes; and monoesters, diesters, and triesters of perfluoroalkyl phosphates and fluorinated ester oils;
   wheatgerm, maize, sunflower, shea, castor, sweet almond, macadamia, apricot, soybean, rapeseed, cottonseed, lucern, poppy seed, pumpkin seed, sesame, gourd, avocado, hazelnut, grape seed, blackcurrant seed, evening primrose, millet, barley, quinoa, olive, rye, safflower, candlenut, passion flower, and musk rose oils; and
   triglycerides of caprylic/capric acids;
   oleic, linoleic, and linolenic acids;
   oleyl alcohol and octyldodecanol;
   paraffin oils and derivatives thereof, petroleum jelly, polydecenes, hydrogenated polyisobutenes, and mixtures thereof;
   linear or branched, volatile or non-volatile $C_6$-$C_{48}$ alkanes;
   linear or cyclic volatile polydimethylsiloxanes (PDMS) comprising from 3 to 7 silicon atoms;
   non-volatile silicone oils chosen from polydimethylsiloxanes (PDMS), polyalkylmethylsiloxanes comprising at least one group chosen from alkyl, alkoxy, and phenyl groups comprising from 2 to 24 carbon atoms, which may be pendant and/or at the silicone chain end; dimethicone copolyols, alkylmethicone copolyols, cetyldimethicone, silicones having alkylglyceryl ether groups, silicones having amine side groups and dilauroyltrimethylol propane siloxysilicate; phenylated silicones, silicones having alkylglyceryl ether groups, silicones having amine side groups, fluorinated silicones having at least one group chosen from pendant groups and groups at the chain end comprising from 1 to 12 carbon atoms in which all or part of the hydrogen atoms are substituted with fluorine atoms, dimethiconols and/or mixtures thereof; and mixtures thereof.

9. The composition of claim 8, wherein:
   the $C_8$-$C_{48}$ esters are chosen from purcellin oil (cetostearyl octanoate); isononyl isononanoate; isopropyl myristate; 2-ethylhexyl palmitate; 2-octyldodecyl stearate; 2-octyldodecyl erucate; isostearyl isostearate; heptanoates, octanoates, decanoates, and ricinoleates of alcohols and polyalcohols; and isopropyl N-lauroylsarcosinate; and/or
   the linear or cyclic polydimethylsiloxanes are chosen from octyltrimethicone, hexyltrimethicone, decamethylcyclopentasiloxane (or D5), octamethylcyclotetrasiloxane (or D4), dodecamethylcyclohexasiloxane (or D6), decamethyltetrasiloxane (or L4), heptamethyloctyltrisiloxane, dodecamethylpentasiloxane, poly-methylcetyldimethylsiloxane; fluorinated silicone oils, silicones having oxyethylenated/oxypropylenated (OE/PP) side groups and having perfluorinated groups, silicones having perfluorinated or polyfluorinated side groups and having glycerolated side groups, and perfluoroalkylmethylphenylsiloxanes; and/or
   the non-volatile silicone oils are chosen from phenyl trimethicones, phenyl dimethicones, phenyl trimethylsiloxy diphenylsiloxanes, diphenyl dimethicones, diphenyl methyldiphenyl trisiloxanes, 2-phenylethyl trimethylsiloxysilicates, and cetyldimethicone.

10. The composition of claim 1, wherein the at least one liquid fatty phase comprises at least one lipophilic compound chosen from:
   $C_6$-$C_{32}$ monoalcohols; $C_6$-$C_{32}$ branched alkanes; $C_{13}$-$C_{48}$ linear alkanes; bifunctional oils, comprising two functional groups chosen from esters and/or amides and comprising from 6 to 30 carbon atoms and 4 heteroatoms chosen from O and N; $C_8$-$C_{48}$ esters, optionally comprising in their hydrocarbon chain at least one heteroatom chosen from N and O and/or at least one carbonyl functional group; volatile or non-volatile silicone oils chosen from linear or cyclic polydimethylsiloxanes (PDMS) comprising from 3 to 7 silicon atoms and mixtures thereof.

11. The composition of claim 10, wherein the $C_6$-$C_{32}$ monoalcohols are chosen from octyldodecanol; the $C_6$-$C_{32}$ branched alkanes are chosen from isododecane and parleams of formula —$(CH_2$—$CH(CH_3))_n$—, wherein n is an integer ranging from 4 to 8;

the bifunctional oils are chosen from isopropyl N-lauroyl-sarcosinate of the following formula:

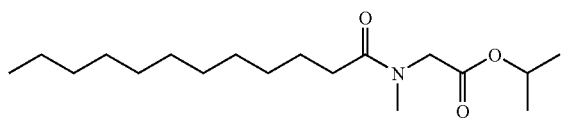

the $C_8$-$C_{48}$ esters are chosen from purcellin oil (cetostearyl octanoate); isononyl isononanoate; isopropyl myristate; 2-ethylhexyl palmitate; 2-octyldodecyl stearate; 2-octyldodecyl erucate; isostearyl isostearate; heptanoates, octanoates, decanoates, and ricinoleates of alcohols and polyalcohols; and/or the volatile or non-volatile silicone oils are chosen from decamethylcyclopentasiloxane, octamethylcyclotetrasiloxane, dodecamethylcyclohexasiloxane and decamethyltetrasiloxane; and phenylated silicones.

12. The composition of claim 5, wherein the at least one lipophilic compound is present in the composition in an amount ranging from 20 to 100% by weight relative to the total weight of the liquid fatty phase.

13. The composition of claim 12, wherein the at least one lipophilic compound is present in the composition in an amount ranging from 60 to 95% by weight relative to the total weight of the liquid fatty phase.

14. The composition of claim 1, further comprising at least one additional constituent chosen from waxes, pasty compounds, water, water-miscible organic solvents; organic or inorganic colorants; fillers, vitamins, thickeners, gelling agents, trace elements, emollients, sequestrants, perfumes, alkalifying or acidifying agents, preservatives, sunscreens, surfactants, antioxidants, antihair-loss agents, antidandruff agents, propellants, ceramides, polymers, cosmetic active agents, and mixtures thereof.

15. A method for the cosmetic treatment of the skin of the body, the skin of the face, lips, nails, eyebrows, hair, eyelashes and/or scalp comprising applying to keratin at least one cosmetic composition comprising, in a physiologically acceptable medium, at least one fatty phase and at least one compound chosen from the following compounds, salts thereof, isomers thereof, and mixtures thereof:

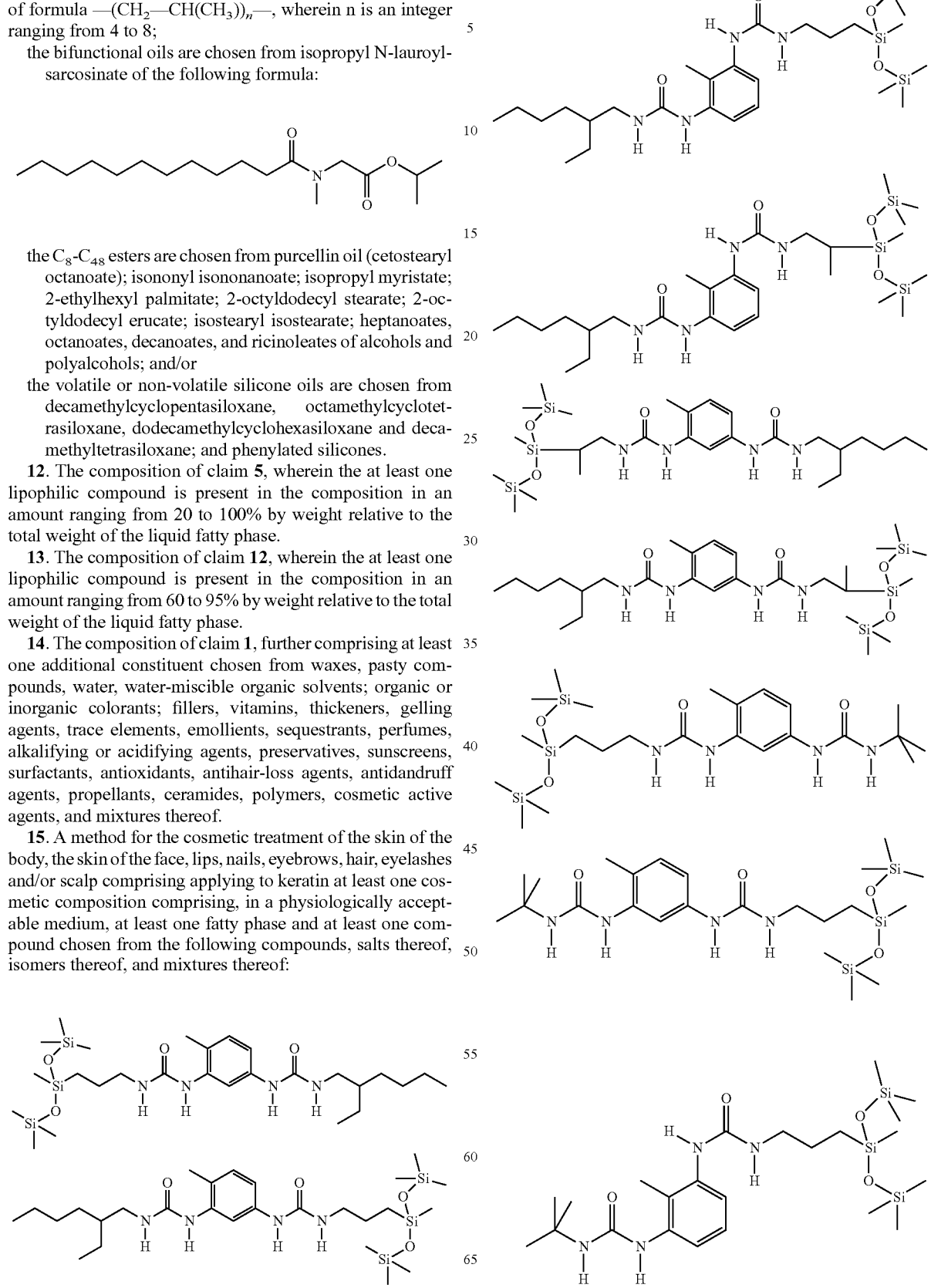

-continued
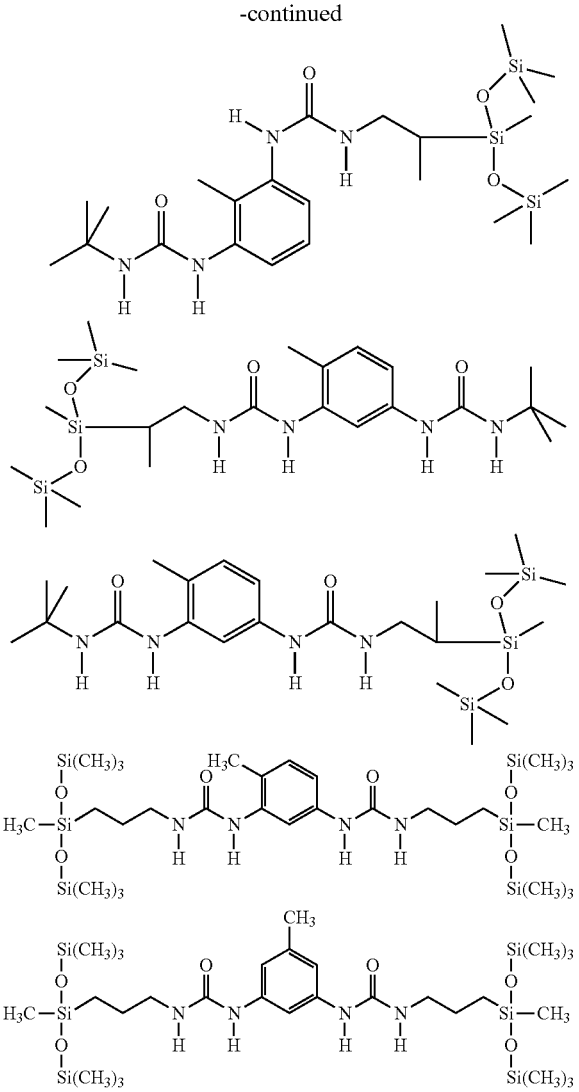
-continued
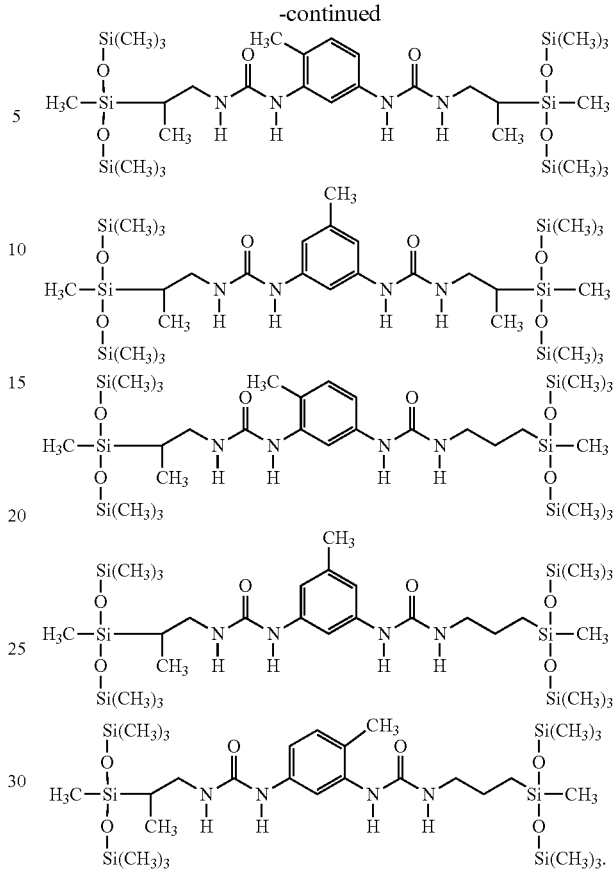
16. The method of claim 15, wherein the treatment is a method for making-up, cleansing, shaping, dyeing, and/or caring for keratin and/or for protecting keratin materials from the sun.
* * * * *